United States Patent [19]

Naderi

[11] Patent Number: 4,955,713

[45] Date of Patent: Sep. 11, 1990

[54] SPECTACLES FOR IMPROVING BINOCULAR VISION

[76] Inventor: Mohammad T. Naderi, Isabellaland 896 2591 ST, The Hague, Netherlands

[21] Appl. No.: 260,272

[22] Filed: Oct. 20, 1988

Related U.S. Application Data

[63] Continuation-in-part of Ser. No. 73,644, Jul. 15, 1987, abandoned.

[51] Int. Cl.[5] .................................... A61B 3/00

[52] U.S. Cl. .................................... 351/200; 351/203

[58] Field of Search .................... 351/41, 45, 44, 46, 351/200, 201, 202, 203; 350/139, 140

[56] References Cited

U.S. PATENT DOCUMENTS 2,396,510 3/1946 Hulst .................................... 350/139

4,790,643 12/1988 Grandiere .......................... 351/200

*Primary Examiner*—Rodney B. Bovernick

*Assistant Examiner*—P. M. Dzierzynski

[57] ABSTRACT

A spectacle for promoting even sight strength in the two eyes comprises a frame, two viewing lenses and a rectangular plate attachment to the frame. The rectangular plate has a bar and a ball affixed to the bar, mounted within a socket located in the frame which can deflect the rectangular plate toward the left lens or the right lens.

3 Claims, 1 Drawing Sheet

SPECTACLES FOR IMPROVING BINOCULAR VISION

RELATED APPLICATIONS

This application is a continuation-in-part of application Ser. No. 073,644, now abandoned filed July 15, 1987.

FIELD OF THE INVENTION

This invention relates to spectacles and, particularly, to a novel spectacle construction for dividing the viewing screen between the two eyes of an observer.

BACKGROUND OF THE INVENTION

Because some people have one eye stronger than the other, they naturally tend to use their strong eye more than their weak eye. Consequently, with passage of time, the weak eye becomes even weaker. In order to alleviate this problem, magnifying glasses have been used to help the weak eye and to restore evenness in sights in the two eyes. However, the use of magnifying glass is not always effective and does not eliminate the tendency of looking through the strong eye. In some cases, in order to strengthen the weak eye, it has been recommended to close the strong eye and look solely through the weak eye. But this procedure is both impractical and cumbersome.

In applicant's application, Ser. No. 717,432, filed Mar. 5, 1985, entitled "Electric Eye Glasses to Strengthen and Exercise the Muscles and Nerves of a Weak Eye," now abandoned, applicant describes a spectacle in which a curtain intermittently closes and opens the glasses on the strong eye, thus causing the weak eye to be more active. However, it is preferable if both eyes were active simultaneously, and hence it is desirable to provide spectacles which afford the ability to see through both eyes simultaneously while eliminating or improving difficulties which have been heretofore described.

Accordingly, it is an object of the present invention to provide spectacles which cause the weak eye to be more active and hence afford equillibrium in both eyesights.

The foregoing and other objects of the invention will become more evident from the ensuing detailed description of the invention and the accompanying drawings.

SUMMARY OF THE INVENTION

A spectable has a rectangular plate member on the outer part of the frame in such a way that its length will be parallel to the nose of the user and could be deflected toward the right eye or the left eye. By wearing the spectacles and looking at a screen, like the screen of a television, and turning the face or the rectangular plate, two different positions can be created. In one position the right eye can see all the area of the screen of the television and the left eye, because of prevention by the rectangular plate, can see only a part of the screen; and in the other position, contrary to the first position, the left eye can see all the area of the screen of the television and the right eye, because of the prevention by the rectangular plate, can see only part of the screen. So by putting on the spectacles, one can force his weak eye to work. The rectangular plate may be transparent to the extent that the sight of the stronger eye, when it is looking through the rectangular plate, is less than the sight of the weaker eye, when it is not looking through the rectangular plate. In this case, the weak eye in the part of the screen which could be seen only by it, without the prevention of the rectangular plate, could see better than the strong eye which is looking to that part through the rectangular plate. Because of the susceptibility of looking through the better eye, the weak eye will look to that part of the screen and the strong eye will help it through the rectangular plate with less sight. But in the part of the screen which could be seen by the two eyes, without the prevention of the rectangular plate, because of the susceptibility of looking through the better eye, this eye will look to that part of the screen and the weak eye, because it is in the active position, will help it with less sight. Therefore, the two eyes work and help each other simultaneously.

BRIEF DESCRIPTION OF THE DRAWINGS

In the drawings, wherein, like numerals are employed to designate like parts.

DETAILED DESCRIPTION OF THE INVENTION

Figure 1:
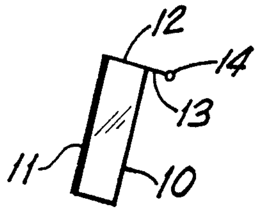
FIG. 1. is a front view of a rectangular plate and ball arrangement used to affix to a spectacle in accordance with the present invention.

Referring to the drawings, and first to FIG. 1, there is shown the rectangular plate 10 which is used to divide a viewing screen, e.g., the television screen. The rectangular plate 10 is approximately 3 centimeters wide and about 10 centimeters long. It is generally of the same color as the color of the nose of the user of the spectacles, or it may be colorless. It is light weight and made of an elastic material so as to avoid injury in case of accident. It may be transparent by varying degrees for different users, the degree of transparentcy varying from 0 to 100 percent.

Along its upper longitudinal edge, the rectangular plate 10 is defined by the line 11, approximately 2 mm., which is not transparent so that the eye cannot see through this line. Thus, the line 11 is useful for dividing the screen properly between the two eyes of the user.

Extending from the upper edge 12 of the rectangular plate 10 is a bar 13 with a ball 14 affixed to the end of the bar.

Figure 2:
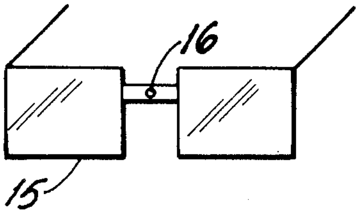
FIG. 2. is a front view of a spectacle according to the present invention having a bridge socket in which the rectangular plates of FIG. 1 can be fixed.
Figure 3:
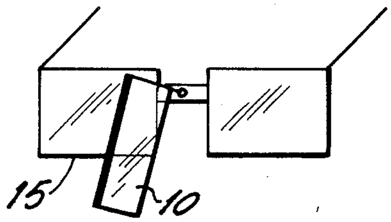
FIG. 3. is similar to FIG. 2. with the rectangular plate fixed to the spectacle as shown.

Referring now to FIG. 2, there is shown a spectacle 15 with a bridge socket 16 in which is fixed the bar 13 with its ball 14 such that the ball 14 is movable within the socket 16. Consequently, the rectangular plate 10 can be turned to the right or left. FIG. 13 shows the spectacle with the rectangular plate affixed as aforesaid.

If one puts on the spectacles and looks to the screen of a television in a position so that he could see the line 11 in the miidle of the screen, he could see all the screen with one eye without the prevention of the rectangular plate 10, and half of the screen without the prevention of the rectangular plate 10 by his other eye. Now if he turns his face in the direction of the eye which could see all the screen without the prevention of the rectangular plate 10, in a moment he will see the line 11 in the middle of the screen. In this position his eye, which in the first position could see all of the screen without the prevention of the rectangular plate 10, now can see only half of it without the prevention of the rectangular plate 10, and his other eye, which at first position could see half of the screen without prevention of the rectangular plate 10, now could see all the screen without the prevention of the rectangular plate 10. Therefore, using the spectacles could create two different positions. In one position the left eye could see all the area of the screen without the prevention of the rectangular plate 10 and could see half of the screen with the right eye without the prevention of the rectangular plate 10 (FIG. 4); in the other position, the right eye could see all of the area of the screen without the prevention of the rectangular plate 10, and half of the screen with the left eye without the prevention of the rectangular plate 10 (FIG. 5).

Figure 6:
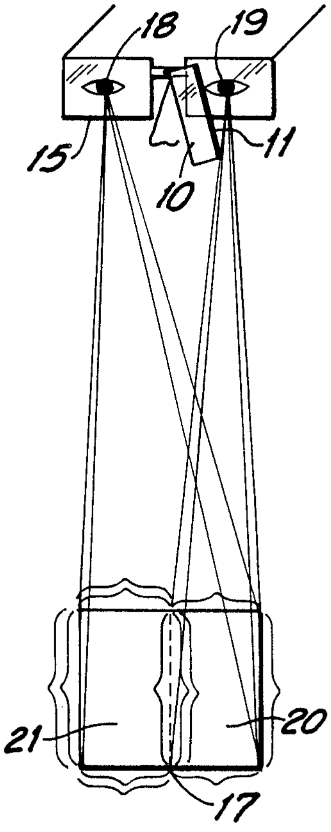
FIG. 6. is a view similar to FIG. 4, in use while looking at a television screen, with the rectangular plate turned toward the left eye so the right eye sees all the screen but the left eye sees only one half of the screen.

In order to create different positions, instead of turning the face in the direction of the eye which could see all the screen without the prevention of the rectangular plate, the rectangular plate may be turned in the direction of the eye which could see all the screen without the prevention of the rectangular plate 10. Referring to FIG. 6, the face is not turned in the direction of the left eye, but instead the rectangular plate 10 is turned in the direction of the left eye.

Figure 4:
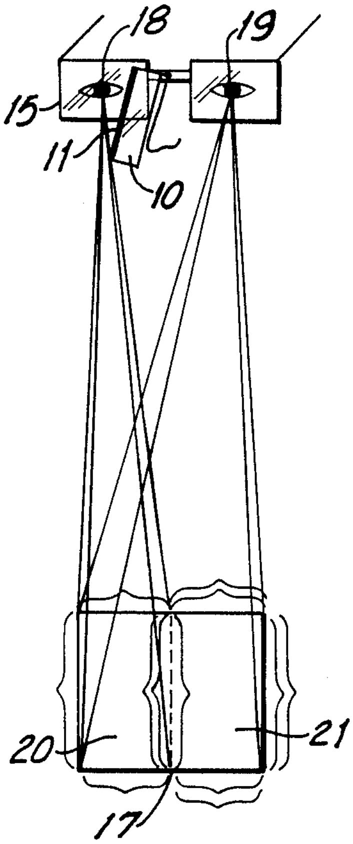
FIG. 4. is a front view of the spectacle of FIG. 3, in use, wherein the user sees all the screen with his left eye and sees half of the screen with the right eye.

Referring back to FIG. 4, it can be seen that the rectangular plate 10 prevents the right eye 18 from seeing the complete area of the screen 17. So the right eye 18 could see only half the screen 17, but the rectangular plate 10 does not prevent the left eye 19 from seeing the screen 17, and the left eye 19 could see all the area of the screen 17. So the screen 17 has two separate parts; one part 20 which could be seen by the two eyes without prevention of the rectangular plate 10 and is shown by four arrows, here called common area 20, and another part 21 which can only be seen by the left eye 19 without prevention of the rectangular plate 10 and is shown by four double arrows, here called special area 21. The position shown in FIG. 4 is proper for the person whose left eye is lazy and does not work. In this position, the left eye 19 is able to see without prevention of the rectangular plate 10, the special area 21 of the screen 17, and is also able to see common area 20 without prevention of the rectangular plate 10. In this position, the right eye 18 could see the special area 21 through the transparent rectangular plate 10 with less sight, in comparison with the left eye 19, (the rays of light passing through the rectangular plate 10 toward the right eye 18 are not shown in FIG. 4 for the sake of clarity in the drawing). Thus, in this position, one who is looking to the screen 17 as the result of susceptibility of looking through the strong eye will look to special area 21 of the screen 17 by his left eye 19 and his right eye 18 through the rectangular plate 10 will help it, and in common area 20 of the screen 17 as the result of the susceptibility of looking through the right eye which, in this position, is stronger than the left eye will look at the screen 17 and the left weak eye 19 because is in active position will help it, consequently the two eyes work and help each other simultaneously.

Figure 5:
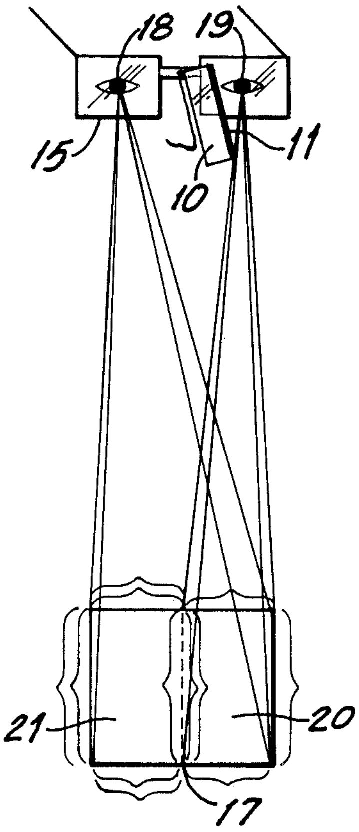
FIG. 5. is a view similar to FIG. 4 with the rectangular plate in different position wherein the user can see all the screen with his right eye.

Now referring to FIG. 5, a different position of looking at the screen 17 is shown. In FIG. 5, contrary to FIG. 4, the rectangular plate 10 prevents the left eye 19 from seeing all of the area of the screen 17 and the left eye 19 could see only half of the area of the screen 17. In the position shown in FIG. 5, the rectangular plate 10 does not prevent the right eye 18 from seeing the screen 17 and right eye 18 could see all the area of screen 17. This position is proper for the person whose right eye is lazy and with less sight in comparison with his left eye. In this position, the right eye 18 is able to see without prevention of the rectangular plate 10, the special area 21 of the screen 17, and the left eye 19 can see the special area 21 through the transparent rectangular plate 10 with less sight in comparison with the right eye 18 (the rays of the light passing through rectangular plate 10 towards the left eye 19 is not shown in FIG. 5 for the sake of clarity in the drawing). So, in this position, one who is looking at screen 17 as the result of susceptibility of looking through his better sight eye will look at the special area 21 of the screen 17 by the right eye 18, and the left eye 19, which in this position, its sight is greater than the right eye 18 through the rectangular plate 10 will help it and in common area 20 as the result of susceptibility of looking by the better sight eye, the left eye 19, which in this position, its sight is greater than the right eye 18 will look at screen 17 and the right eye 18 because it is in active position will help the left eye 19. Consequently, the two eyes work and help each other simultaneously.

If the rectangular plate 10 is not transparent the situation will be different, and only the weak eye could see the special area.

What is claimed is:

1. A spectacle which divides a screen between the eyes of an observer comprising a spectacle frame and two viewing lenses, said spectacle further comprising a socket centrally mounted on the outer part of said spectacle frame, a rectangular plate member defined by two elongated sides and two short edges, a bar member extending from one of said short edges of said rectangular plate member and a ball member fixed at the end of said bar member, said ball member being disposed within said socket, said rectangular plate member being deflectable toward the left lens and the right lens by said bar member and said ball member.

2. A spectacle as recited in claim 1 wherein said rectangular plate member is transparent.

3. A spectacle as recited in claim 1 wherein said rectangular plate member has a flesh color.

* * * * *